(12) United States Patent
Strobel

(10) Patent No.: US 7,050,844 B2
(45) Date of Patent: May 23, 2006

(54) METHOD FOR DETECTING THE THREE-DIMENSIONAL POSITION OF A MEDICAL EXAMINATION INSTRUMENT INTRODUCED INTO A BODY REGION, PARTICULARLY OF A CATHETER INTRODUCED INTO A VESSEL

(75) Inventor: Norbert Strobel, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 472 days.

(21) Appl. No.: 10/104,711

(22) Filed: Mar. 22, 2002

(65) Prior Publication Data

US 2003/0014034 A1 Jan. 16, 2003

(30) Foreign Application Priority Data

Mar. 22, 2001 (DE) ................................ 101 14 099

(51) Int. Cl.
*A61B 5/05* (2006.01)

(52) U.S. Cl. ........................ 600/424; 600/427; 606/130

(58) Field of Classification Search ................ 600/427, 600/424; 378/21–27; 606/130
See application file for complete search history.

(56) References Cited

U.S. PATENT DOCUMENTS

| 5,923,727 | A | * | 7/1999 | Navab ......................... 378/207 |
| 6,104,780 | A | * | 8/2000 | Hanover et al. ............... 378/92 |
| 6,149,592 | A | * | 11/2000 | Yanof et al. ................. 600/427 |
| 6,317,621 | B1 | | 11/2001 | Graumann et al. .......... 600/424 |
| 6,370,417 | B1 | | 4/2002 | Horbaschek et al. ......... 600/424 |
| 6,542,770 | B1 | * | 4/2003 | Zylka et al. ................. 600/424 |

* cited by examiner

*Primary Examiner*—Brian L. Casler
*Assistant Examiner*—Julianne M. Sullivan
(74) *Attorney, Agent, or Firm*—Schiff Hardin LLP

(57) ABSTRACT

In a method for detecting the three-dimensional position of a medical examination instrument introduced into an examination region of a subject and an apparatus including a C-arm system for registering radiation images, two-dimensional angiography projection images of the examination region are registered for later three-dimensional volume reconstruction of the examination region. After introduction of the instrument, at least one two-dimensional projection image pair of the examination region with image planes residing at an angle relative to one another is registered. The spatial coordinates of a selected point of the instrument shown in the projection images are identified in a common coordinate system for the angiography projection images and the projection images. Two-dimensional projection image pairs are registered in succession for the continuous presentation of the selected point in the display of the aforementioned volume reconstruction.

26 Claims, 2 Drawing Sheets

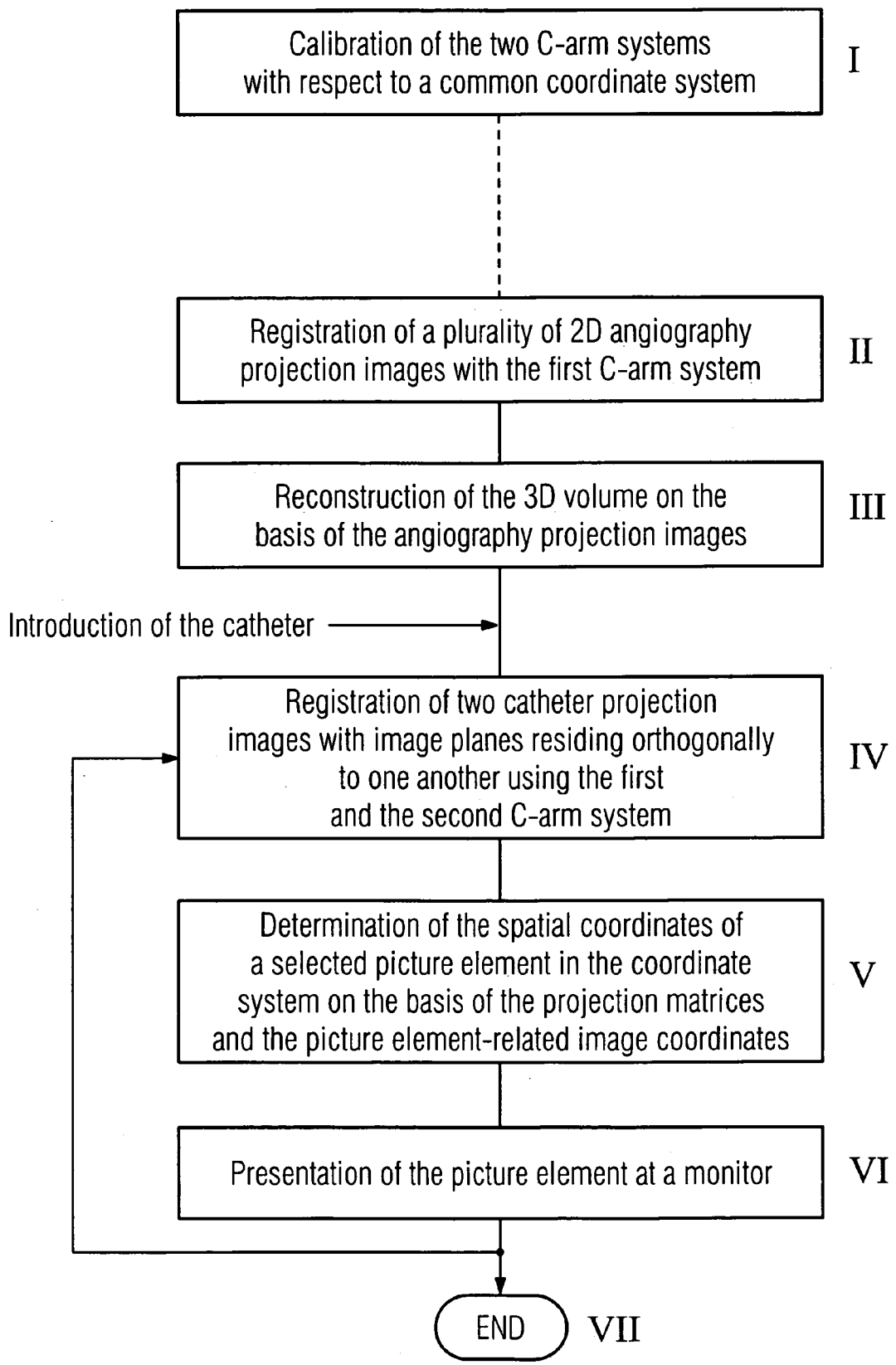

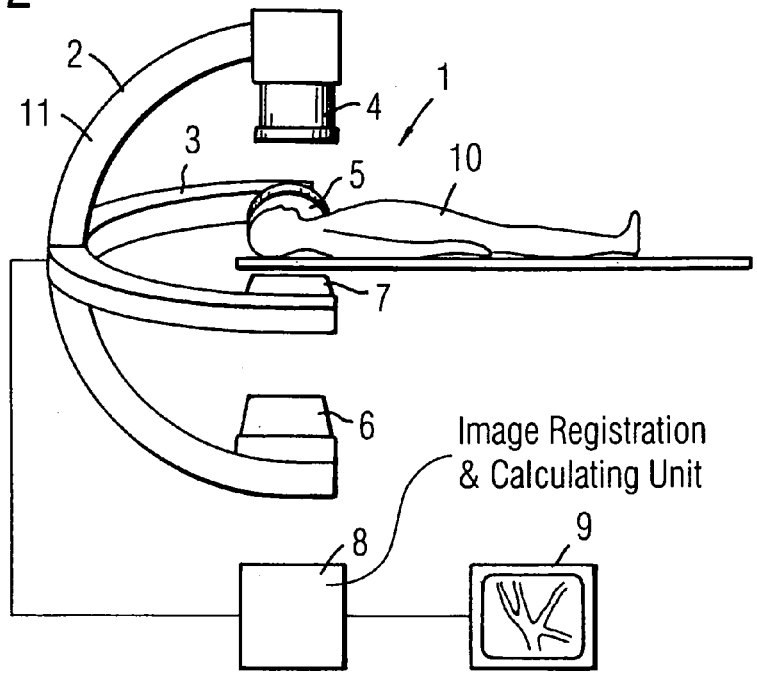
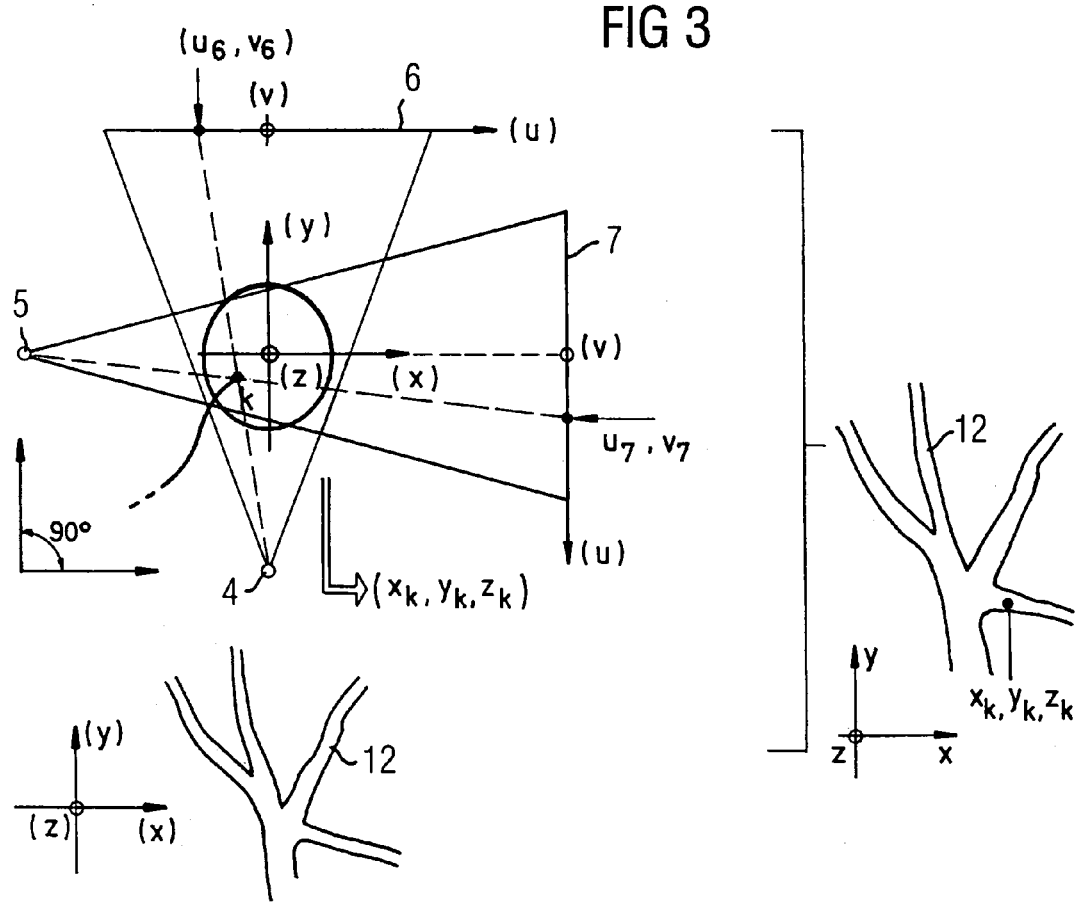

METHOD FOR DETECTING THE THREE-DIMENSIONAL POSITION OF A MEDICAL EXAMINATION INSTRUMENT INTRODUCED INTO A BODY REGION, PARTICULARLY OF A CATHETER INTRODUCED INTO A VESSEL

BACKGROUND OF THE INVENTION

1. Field of the Invention

The present invention is directed to a method for automatically detecting the three-dimensional position of a medical examination instrument introduced into a body region, particularly a catheter introduced into a vessel, using a device for registering radiation images having at least one C-arm system having a C-arm with a radiation source and a radiation receiver.

2. Description of the Prior Art

To allow a physician who, for example, sets a catheter to push it into the desired target region, it is necessary that the physician receive information about the respective position or, attitude of the catheter during the displacement. The physician is basically interested only in the position of the catheter tip, whose position and alignment define the further course of motion. Conventionally, the physician has received the relevant information on the basis of transillumination images of the examination region registered with an x-ray system. Usually, transillumination images are continuously registered from two different directions, with two image planes residing at an angle relative to one another. These are presented to the physician side-by-side at a common monitor or at two side-by-side monitors. On the basis of these two images, whose image planes are usually perpendicular to one another, the physician can identify the position of the catheter in the vessel and recognize how the catheter moves in space. A disadvantage, however, is that the physician must simultaneously look at two monitors or, two images in order to obtain the required information. Another disadvantage is that the two images are merely projection images, i.e., all body parts in the projection direction are superimposed on one another. As a result, it is complicated for the physician to recognize the actually established three-dimensionally geometry on the basis of these two two-dimensional projection images, particularly when the vessel branches in an extremely irregular way.

German OS 199 19 907 discloses a method for catheter navigation in three-dimensional vessel tree exposures, particularly for intra-cranial application. A position acquisition system is utilized for acquiring the catheter position, this being positioned in the tip of the catheter and a number of markers situated at the patient and transmission coils located externally relative to the patient. The markers situated at the patient serve the purpose of defining a patient coordinate system wherein the catheter position in this coordinate is identified using the transmission coils and the position acquisition system in the catheter tip. The actual vessel tree is registered in an image coordinate system; two different coordinate systems are thus utilized therein, these being registered relative to one another using transformation matrices. For registration, there is the possibility of making use of two-dimensional projection images of the vessel tree that were pre-operatively registered and already exist, the markers serving the purpose of registration being acquired therein, with the markers being projected back onto the imaged object and brought into relationship with the marker coordinates in the patient coordinate system using the projection matrices that exist for the respective two-dimensional projection images, these projection matrices having been determined for the reconstruction of the three-dimensional volume set.

Further, German PS 198 43 408 provides a method for reproduction of x-ray images with the assistance of an x-ray device when positioning a catheter introduced into a vessel. In this method, first, a number of two-dimensional individual images are registered from different directions and a three-dimensional image dataset is subsequently generated; a three-dimensional image is determined based thereon and reproduced, this showing the vessel. Thereafter, a second two-dimensional individual image of the vessel with introduced catheter is generated from a specific registration direction. Subsequently, a two-dimensional mask image is generated from the three-dimensional image dataset, the registration direction of the mask image corresponding as best as possible to the exposure direction of said two-dimensional individual image. Subsequently, the generated mask image is combined with the registered, second two-dimensional individual image to form a combination image of the vessel with catheter introduced therein. This combination image is subsequently output in order to be able to identify the catheter position in the vessel on the basis thereof.

SUMMARY OF THE INVENTION

An object of the present invention is to provide a method that allows the physician to simply recognize the position of the instrument in the body, particularly a catheter in the vessel, as well as enabling a simple orientation.

This object is achieved in a method of the type initially described wherein a number of two-dimensional angiography projection images are obtained of the examination region into which the instrument is to be introduced, for later three-dimensional volume reconstruction of the examination region, after introduction of the instrument. At least one two-dimensional projection image pair of the examination region is obtained with image planes residing at an angle relative to one another. The spatial coordinates of a selected point of the instrument shown in the projection images are identified in a common coordinate system for the angiography projection images and the projection images. The selected point of the instrument is presented within the three-dimensional volume reconstruction of the examination region in the common coordinate system at a monitor, and two-dimensional projection image pairs are obtained continuously or discontinuously in succession so that the selected point of the examination instrument located in the examination region is continuously presented on the monitor.

A particular advantage of the inventive method is that it offers the possibility of displaying the selected point, for example the catheter tip, within a three-dimensional presentation of the examination region, i.e. of the vessel tree in which the catheter is introduced. The physician thus is presented with a three-dimensional image of the anatomical conditions, wherein the physician can immediately recognize the position and the further course of the motion of the catheter.

According to the inventive method, a 3D angiography of the examination region is implemented first for this purpose. To this end, a sequence of two-dimensional angiography images is registered using the C-arm system, the three-dimensional volume of the examination region being reconstructed later on the basis thereof. This 3D angiography occurs before the setting of the catheter; subsequently, the catheter is introduced, whereupon two-dimensional projection image pairs of the examination region are registered either continuously or discontinuously, the catheter being visible therein and these having image planes residing at an angle relative to one another. The angiography projection images as well as the projection images are based on a common coordinate system, i.e. it is subsequently possible to calculate the spatial coordinates of a selected catheter point, i.e., for example, of the catheter tip, on the basis of the catheter images. These spatial coordinates simultaneously indicate the position of the catheter tip in the volume structure obtained from the 3D angiography. To this end, it is necessary that the patient not move during the examination.

In order to achieve this coordinate consistency, the projection matrices of the C-arm positions, at which the angiography images are obtained and the projection matrices of the C-arm positions, at which the projection images with the catheter are obtained, are calibrated with respect to a common coordinate system or a common coordinate origin. The projection matrices that describe the position of the C-arm in the space are the basis of the three-dimensional reconstruction as well as of the determination of the spatial coordinates of the catheter tip. There is a projection matrix for each C-arm position, and thus also for each registered image. Since the projection matrices are calibrated with respect to a common coordinate system or, a common system origin for the C-arm positions, at which the angiography projection images are obtained, and the matrices for the C-arm positions wherein the projection images with the catheter are obtained, are calibrated with respect to a common coordinate system or a common system origin, each picture element can consequently be described and presented within the common coordinate system.

It suffices for the calibration to ensue at specific time intervals, for example at intervals of three months. It thus need not be implemented before every examination.

In an embodiment of the invention, an apparatus having only one C-arm system is employed for the implementation of the inventive method, with the angiography projection images as well as the projection images being registered therewith. For this purpose, the C-arm is moved into two different angular positions for registering the projection images with the image planes residing differently relative to one another. In this embodiment of the invention, thus, only one C-arm is present with which the angiography projection images are registered first, with the C-arm rotating around the examination region by at least 180° plus the fan angle. The projection images of the catheter are also subsequently registered with this C-arm. When the physician requests an image exposure, a first catheter projection image is registered first, whereupon the C-arm is pivoted by, preferably, 90°, and the second catheter projection image of the image pair is registered. During this time, the catheter must not be moved. Although only a discontinuous acquisition of the catheter position is possible with this version of the method since the C-arm must be pivoted into two positions for each position determination while the catheter remains stationary, it is nonetheless possible for the physician to make an exact determination of the momentary position of the catheter even in this simple embodiment of the invention.

In an alternative embodiment of the invention, an apparatus having two C-arm systems residing at an angle relative to one another is employed for the registration. A first image of a projection image pair is registered with one C-arm system and a second image of the image pair is registered with the other C-arm system, with both C-arm systems being calibrated with respect to the same coordinate system, i.e. the respective projection matrices describing the positions of the C-arm for the respective, registered image are calibrated with respect to the same coordinate system. Due to the calibration of the projection matrices, a coordinate consistency that allows an exact description of the relevant positions in the common coordinate system is established even with the use of different C-arm systems.

The calibration of the two C-arm systems in this case ensues such that the first C-arm system is first placed relative to a calibration phantom that is placed into the beam path between the radiation source and the radiation receiver of the first C-arm system. The respective projection matrices that are specific for the arcuate position are identified and the isocenter is calculated on the basis of these. Subsequently, the second C-arm system is calibrated with respect to the same calibration phantom and the corresponding projection matrices are registered. Both C-arm systems can be of a type referred to as a bi-plane C-arm system wherein two C-arms residing orthogonally relative to one another are arranged (usually) at a common carrier. Alternatively, these two systems can be separate systems with one, for example, mounted at the ceiling side and the other mounted at the floor, these being not only rotatable relative to one another but also being longitudinally displaceable.

With the use of two C-arm systems, a continuous registration of projection image pairs is possible, i.e. the physician is presented with the continuously occurring displacement motion of the instrument position. In addition of course, an image registration at predetermined time intervals is possible.

With an apparatus having two C-arm systems, the angiography projection images themselves can be registered with only one C-arm system. Due to the calibration of the projection matrices with respect to the common coordinate system, however, it is also possible to register the angiography projection images with both C-arm systems. The determination of the selected point itself expediently is accomplished by subtraction of time-successive projection images that were registered at the same detector.

In addition to the inventive method, the invention is also directed to an apparatus for the registration of radiation images, having at least one C-arm system with a C-arm having a radiation source and a radiation receiver, and an image registration and calculating arrangement. The image registration and calculating arrangement reconstructs a three-dimensional volume of a registered examination region on the basis of a plurality of registered two-dimensional angiography projection images, determines the spatial coordinates of a selected point of an instrument introduced into the examination region and shown in two registered projection images whose image planes reside at an angle relative to one another, namely in a common coordinate system on which the registration of the angiography projection images and of the projection images is based, presents the selected point of the instrument within the three-dimensional volume reconstruction of the examination region in the common coordinate system at a monitor, and in the two-dimensional projection image pairs can be registered continuously or discontinuously in succession and the spatial coordinates can be identified for continuous presentation of the selected point of the examination instrument located in the examination region.

The inventive apparatus is thus fashioned for the implementation of the above-described method.

In a first embodiment of the inventive apparatus, only one C-arm system is provided for registering both the angiography projection images and the instrument projection images. The C-arm can be moved into two different annular positions for the registration of the instrument projection images. Both the image registration and the movement of the C-arm are controlled via the image registration and calculating arrangement which, for example, can be a central control device wherein all relevant operations of the apparatus are controlled and processed.

Alternatively, the apparatus can also have two C-arm systems residing at an angle relative to one another, with a first image of the projection image pair being registered with one C-arm system and a second projection image being registered with the other C-arm system. In this case, the projection matrices of the C-arm positions, wherein the angiography projection images are registered, and the projection matrices of the C-arm position wherein the instrument projection images are registered are expediently calibrated with respect to a common coordinate system.

The image registration and calculating arrangement can be fashioned for continuous image registration or for image registration at predetermined time intervals, as well as for a determination of the coordinates of the selected point virtually immediately after the respective registration and the presentation thereof at the monitor within the reconstruction volume.

The image planes of the catheter images preferably reside orthogonally relative to one another. In order to achieve this, only one C-arm system can be moved into two positions residing orthogonally relative to one another for the registration of the projection images of an image pair, or the two C-arm systems can be disposed orthogonally relative to one another in the aforementioned alternative apparatus embodiment. In this latter apparatus embodiment, a bi-plane C-arm system having two C-arms arranged at a common carrier can be provided; alternatively, two separate C-arm systems can be utilized.

DESCRIPTION OF THE DRAWINGS

FIG. 1 is a flow chart for explaining the inventive method.
FIG. 2 is a schematic-diagram of an inventive apparatus.
FIG. 3 is a schematic diagram for explaining the generation of the three-dimensional presentation of the examination region with the selected point.

DESCRIPTION OF THE PREFERRED EMBODIMENTS

FIG. 1 shows the executive sequence of the inventive method as a flow chart. In Step I, a calibration of the two C-arm systems with respect to a common coordinate system ensues first, with the two C-arm systems being moved into different positions around a calibration phantom, and the position-related projection matrices being acquired. This calibration ensues, for example, at intervals of a quarter-year or semi-annually.

An examination of a patient is initiated in Step II. The patient, lying on a patient support, is moved into the beam path of the two C-arm systems with the examination region. For example, a patient's brain, into which a catheter is to be inserted, can be registered as the examination region.

According to Step II, a 3D angiography is first implemented, a number of two-dimensional angiography projection images being registered during the course thereof with one or both C-arm systems. A reconstruction of the three-dimensional volume of the examination region, i.e. of the brain in this case, or of a vessel tree of interest in the brain, ensues in Step III on the basis of these two-dimensional angiography projection images.

The catheter is subsequently introduced. In Step IV, two projection images are registered with both C-arm systems having image planes that reside orthogonally relative to one another due to the orthogonal arrangement of the two C-arm systems with respect to the same coordinate system. On the basis of these two-dimensional projection images, the spatial coordinates of a selected picture element of these two images, namely of the tip of the catheter shown in the images, are determined in Step V. These are determined in the common coordinate system on the basis of the projection matrices as well as on the basis of the picture element-related image coordinates, i.e. the coordinates of the two projection images that describe the position of the picture element in the image. In Step VI, first, the reconstructed 3D volume of the vessel tree as well as the identified point that describes the position of the catheter tip are displayed at a monitor. The physician thus exactly sees the spatial position of the catheter tip as well as the spatial course of the vessel into which the catheter tip has been introduced.

Steps IV–VI are continuously repeated, i.e. a continuous registration of the instrument projection images ensues, resulting in a continuous acquisition of the movement of the catheter in the vessel. After the final positioning of the catheter, the image registration is ended in Step VII.

FIG. 2 shows an inventive apparatus for the implementation of this method, in the form of a schematic diagram. This apparatus 1 has two C-arm systems 2, 3 that, in the illustrated example, are fashioned as bi-plane C-arm systems and are arranged in a common carrier that is not shown in greater detail. Such systems are known; their specific structure need not be discussed in greater detail herein.

The C-arm systems 2 and 3 respectively have radiation sources 4, 5 and radiation detectors 6, 7. The radiation sources 4, 5 are fashioned as x-ray radiators; the radiation detectors 6, 7 are fashioned as x-ray image intensifiers or as flat image detectors.

An image registration and calculating unit 8 is provided for controlling the image registration mode as well as for determining the images to be output, all relevant functions, whether the movement of the C-arms 2, 3 or the control of the radiation sources 4, 5 and the radiation detectors 6, 7. The determination of the coordinates and the actual image determination and output also is controlled with the image registration and calculating unit 8. The image is displayed at a monitor 9.

The registration and determination of the information with the apparatus 1 are shown in FIG. 3 as a schematic diagram.

Before the catheter is introduced into the patient 10, the patient is first placed into the beam paths of the two C-arm systems 2, 3. Subsequently, a 3D angiography of the examination region, of the head in this case, is registered with the C-arm system 2. During the course thereof, the C-arm 11 of the C-arm system 2 rotates through at least 180° plus the cone angle (i.e. the angle that the beam path forms proceeding from the radiation source 4 to the radiation detector 6). A number of two-dimensional angiography projection images are thereby registered. A three-dimensional reconstruction of the vessel tree 12 shown at the bottom in FIG. 3 is made on the basis of these images. The vessel tree 12 is reconstructed in a coordinate system (x, y, z).

Subsequently, the catheter K is introduced. After this, projection images showing the catheter are registered with the two C-arm systems 2, 3 and the position of the catheter tip can be determined in the coordinate system (x, y, z) on the basis of the image pair. In the form of a schematic diagram, FIG. 3 shows the registration of two projection images of an image pair. The two radiation sources 4, 5 are shown, as are the appertaining radiation detectors 6, 7. The examination region, the head of the patient in this case, is located in the beam paths of the x-rays emitted by the radiation sources 4, 5. The radiation sources 4, 5 as well as the detectors 6, 7 reside orthogonally relative to one another. In this way, two projection images residing orthogonally relative to one another are obtained at the detectors 6, 7, the tip of the catheter K being visible therein. The position of this picture element describing the catheter tip on the surface of the detector is described by the coordinates ($u_6$, $v_6$) relating to the radiation detector 6 as well as ($u_7$, $v_7$) relating to the radiation detector 7.

The two C-arm systems 2, 3, which reside orthogonally relative to one another here, but also can assume different angles with respect to one another, are calibrated with respect to a common coordinate system or, calibration phantom. In this procedure, the projection matrices describing the respective positions of the C-arm systems 2 and 3 are calibrated with respect to the same point. Since the angiography projection images were registered with the C-arm system 2 and since the projection images showing the catheter were registered with both C-arm systems 2, 3 that are calibrated with respect to the same coordinate system, it necessarily follows that coordinates that describe points that lie in the coordinate system of the three-dimensional reconstruction of the examination volume can be determined on the basis of the two catheter projection images.

In order to then determine the x, y and z-coordinates of the catheter tip in the coordinate system (x, y, z) of the reconstruction volume, i.e. of the vessel tree 12, the known projection matrices describing the positions of the two C-arm systems 2, 3, as well as the image coordinates ($u_6$, $v_6$) and ($u_7$, $v_7$), are determined. The spatial coordinates ($x_K$, $y_K$, $z_K$) describing the spatial position then can be calculated by matrix calculation.

The reconstruction volume, i.e. the vessel tree 12, as well as the position of the catheter tip with the coordinates ($x_K$, $y_K$, $z_K$), are then displayed at the monitor 9. The display is based on the common coordinate system (x, y, z). On the basis of this display, the physician can recognize the exact spatial position of the catheter tip in the three-dimensionally presented vessel tree 12.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A method for detecting a three-dimensional position of a medical instrument introduced into a body region, using a radiological imaging system having at least one C-arm system with a C-arm having a radiation source and a radiation detector mounted thereon, comprising the steps of:

obtaining a plurality of two-dimensional angiography projection images relative to a coordinate system, using said radiological imaging system, of an examination region into which said instrument is to be introduced, and subsequently producing a three-dimensional volume reconstruction of said examination region from said two-dimensional angiography projection images;

introducing said instrument into said examination region and, after introduction of said instrument, obtaining at least one pair of two-dimensional projection images of said examination region relative to said coordinate system, using said radiological examination system, said two-dimensional projection images in said pair being disposed at an angle relative to each other;

identifying a first set of projection matrices for respective positions of said C-arm when obtaining said angiography images, and identifying a second set of projection matrices for respective positions of said C-arm when obtaining said respective pairs of said two-dimensional projection images, and calibrating said first set of projection matrices and said second set of projection matrices with respect to said coordinate system;

identifying spatial coordinates of a selected point of said instrument in said pair of two-dimensional projection images in said coordinate system;

representing said selected point of said instrument in a visual presentation of said three-dimensional volume reconstruction of said examination region in said coordinate system; and repeatedly obtaining respective pairs of said two-dimensional projection images in sufficiently frequent succession to continuously represent said selected point of said examination instrument in said examination region in said visual representation.

2. A method as claimed in claim 1 comprising repeatedly obtaining said respective pairs of said two-dimensional projection images continuously.

3. A method as claimed in claim 1 comprising repeatedly obtaining said respective pairs of said two-dimensional projection images discontinuously.

4. A method as claimed in claim 1 wherein said radiological imaging system comprises two C-arm systems disposed at an angle relative to each other, and wherein the step of obtaining the pair of two-dimensional projection images and the step of repeatedly obtaining respective pairs or two-dimensional projection images each comprises obtaining a first image of each pair with a first of said two C-arm system and obtaining a second image of each pair with a second of the two C-arm systems, and further comprising calibrating both of said first and second C-arm systems with respect to said coordinate system.

5. A method as claimed in claim 4 comprising visually representing the respective pairs within said three-dimensional reconstruction volume immediately after the respective pairs are obtained.

6. A method as claimed in claim 4 comprising obtaining said first and second two-dimensional images in each pair in respective image planes that are oriented orthogonally relative to each other.

7. A method as claimed in claim 4 comprising obtaining said angiography projection images with only one of said two C-arm systems.

8. A method as claimed in claim 4 comprising obtaining said angiography projection images with both of said two C-arm systems.

9. A method as claimed in claim 4 comprising employing a bi-plane C-arm system to form said two C-arm systems.

10. A method as claimed in claim 4 comprising employing two separate C-arm systems to form said two C-arm systems.

11. A method as claimed in claim 1 comprising obtaining said first and second two-dimensional images in each pair in respective image planes that are oriented orthogonally relative to each other.

12. A method as claimed in claim 1 wherein said medical instrument has an instrument tip, and selecting said instrument tip as said selected point of said medical instrument.

13. A method as claimed in claim 1 comprising determining said selected point by subtracting the respective projection images of one of said image pairs.

14. A medical imaging apparatus for detecting a three-dimensional position of a medical instrument introduced into a body region comprising:

a radiological imaging system having at least one C-arm system with a C-arm having a radiation source and a radiation detector mounted thereon, for obtaining a plurality of two-dimensional angiography projection images relative to a coordinate system of an examination region into which an instrument is to be introduced;

a computer for producing a three-dimensional volume reconstruction of said examination region from said two-dimensional angiography projection images;

said radiological imaging system, after introduction of said instrument, obtaining at least one pair of two-dimensional projection images of said examination region relative to said coordinate system, said two-dimensional projection images in said pair being disposed at an angle relative to each other;

said computer identifying a first set of projection matrices for respective positions of said C-arm when obtaining said angiography images and identifying a second set of projection matrices for respective positions of said C-arm when obtaining said respective pairs of said two-dimensional projection images, and said computer calibrating said first set of projection matrices and said second set of projection matrices with respect to a said coordinate system;

said computer identifying spatial coordinates of a designated point of said instrument in said pair of two-dimensional projection images in said coordinate system applicable to both said angiography projection images and said pair of two-dimensional projection images;

a display connected to said computer;

said computer representing said designated point of said instrument in a visual presentation of said three-dimensional volume reconstruction of said examination region in said coordinate system on said display; and said radiological imaging system repeatedly obtaining respective pairs of said two-dimensional projection images in sufficiently frequent succession to allow said computer to continuously represent said designated point of said examination instrument in said examination region in said visual representation on said display.

15. A medical imaging apparatus as claimed in claim 14 wherein said radiological imaging system repeatedly obtains said respective pairs of said two-dimensional projection images continuously.

16. A medical imaging apparatus as claimed in claim 14 wherein said radiological imaging system repeatedly obtains said respective pairs of said two-dimensional projection images discontinuously.

17. A medical imaging apparatus as claimed in claim 14 wherein said radiological imaging system comprises two C-arm systems disposed at an angle relative to each other, wherein the radiological imaging system obtains the pair of two-dimensional projection images and repeatedly obtains said respective pairs or two-dimensional projection images by obtaining a first image of each pair with a first of said two C-arm system and obtaining a second image of each pair with a second of the two C-arm systems, and wherein said computer calibrates both of said first and second C-arm systems with respect to said coordinate system.

18. A medical imaging apparatus as claimed in claim 17 wherein said computer visually represents the respective pairs within said three-dimensional reconstruction volume on said display immediately after the respective pairs are obtained by said radiological imaging system.

19. A medical imaging apparatus as claimed in claim 17 wherein said radiological imaging system obtains said first and second two-dimensional images in each pair in respective image planes that are oriented orthogonally relative to each other.

20. A medical imaging apparatus as claimed in claim 17 wherein said radiological imaging system obtains said angiography projection images with only one of said two C-arm systems.

21. A medical imaging apparatus as claimed in claim 17 wherein said radiological imaging system obtains said angiography projection images with both of said two C-arm systems.

22. A medical imaging apparatus as claimed in claim 17 wherein said radiological imaging system employs a bi-plane C-arm system forming said two C-arm systems.

23. A medical imaging apparatus as claimed in claim 17 wherein said radiological imaging system comprises two separate C-arm, systems forming said two C-arm systems.

24. A medical imaging apparatus as claimed in claim 14 wherein said radiological imaging system obtains said first and second two-dimensional images in each pair in respective image planes that are oriented orthogonally relative to each other.

25. A medical imaging apparatus as claimed in claim 14 wherein said medical instrument has an instrument tip, and wherein said computer employs said instrument tip as said designated point of said medical instrument.

26. A medical imaging apparatus as claimed in claim 14 wherein said computer determines said designated point by subtracting the respective projection images of one of said image pairs.

* * * * *